US012643293B2

(12) United States Patent
Puce

(10) Patent No.: US 12,643,293 B2
(45) Date of Patent: Jun. 2, 2026

(54) REALIZATION METHOD OF AN ORTHOPEDIC SUPPORT

(71) Applicant: BIOLIBRARY SRLS, Ascoli Piceno (IT)

(72) Inventor: Antonio Puce, Ascoli Piceno (IT)

( * ) Notice: Subject to any disclaimer, the term of this patent is extended or adjusted under 35 U.S.C. 154(b) by 1051 days.

(21) Appl. No.: 17/777,952

(22) PCT Filed: Dec. 2, 2020

(86) PCT No.: PCT/EP2020/084228
§ 371 (c)(1),
(2) Date: May 18, 2022

(87) PCT Pub. No.: WO2021/110725
PCT Pub. Date: Jun. 10, 2021

(65) Prior Publication Data
US 2022/0410484 A1     Dec. 29, 2022

(30) Foreign Application Priority Data

Dec. 3, 2019     (IT) ........................ 102019000022866

(51) Int. Cl.
*B33Y 80/00*          (2015.01)
*A61F 5/01*          (2006.01)
(Continued)

(52) U.S. Cl.
CPC .............. *B29C 64/386* (2017.08); *A61F 5/01* (2013.01); *B22F 10/80* (2021.01); *B33Y 50/00* (2014.12);
(Continued)

(58) Field of Classification Search
CPC .......... B29C 64/386; A61F 5/01; B22F 10/80; B33Y 50/00; B33Y 80/00; G06F 30/10; B29L 2031/753
See application file for complete search history.

(56) References Cited

U.S. PATENT DOCUMENTS 6,932,842 B1     8/2005  Litschko et al.
2010/0076439 A1*  3/2010  Hatch ................ A61B 17/1659
                                            606/79
(Continued)

FOREIGN PATENT DOCUMENTS

CN          106113497 B      12/2018
WO          2017127887 A1     8/2017

OTHER PUBLICATIONS

International Search Report for corresponding PCT/EP2020/084228, dated Mar. 31, 2021.
(Continued)

*Primary Examiner* — Brian W Wathen
(74) *Attorney, Agent, or Firm* — Egbert, McDaniel & Swartz, PLLC

(57)          ABSTRACT

A design method of an orthopedic support suitable for being applied on a part of the body of a patient. The method initially provides for a step of determination of the part of the body where the orthopedic support is to be applied. Next is a step of identification of a generic 3D model relative to the part of the patient's body where the orthopedic support is to be applied. Then, there is a step of acquisition of a 3D image of the part of the patient's body and for a step of detection of biometric data of the part, and finally for a step of modeling of the generic 3D model by merging the generic 3D model with the 3D image in such a way to obtain a 3D model that is modelized based on the morphology of the part of the patient's body.

1 Claim, 1 Drawing Sheet

(51) Int. Cl.

| | | |
|---|---|---|
| B22F 10/80 | (2021.01) | |
| B29C 64/386 | (2017.01) | |
| B33Y 50/00 | (2015.01) | |
| G06F 30/10 | (2020.01) | |
| B29L 31/00 | (2006.01) | |

(52) U.S. Cl.
CPC ........ *G06F 30/10* (2020.01); *B29L 2031/753* (2013.01); *B33Y 80/00* (2014.12)

(56) References Cited

U.S. PATENT DOCUMENTS

| | | | |
|---|---|---|---|
| 2014/0309642 A1* | 10/2014 | Victor ................ | A61B 17/1668 606/84 |
| 2015/0328016 A1 | 11/2015 | Summit et al. | |
| 2017/0202695 A1* | 7/2017 | Zachariasen .......... | B29C 64/386 |
| 2018/0147062 A1* | 5/2018 | Ay ........................... | G06T 17/00 |
| 2018/0185098 A1* | 7/2018 | Buck ......................... | A61F 5/01 |
| 2019/0201228 A1* | 7/2019 | Van Meer .......... | G05B 19/4099 |
| 2020/0100947 A1* | 4/2020 | Moon .................... | B33Y 80/00 |
| 2020/0356073 A1* | 11/2020 | Tokushima ........ | G05B 19/4099 |
| 2021/0070913 A1* | 3/2021 | Sim ......................... | A61L 15/14 |
| 2021/0205099 A1* | 7/2021 | Parr ....................... | A61B 34/10 |

OTHER PUBLICATIONS

Written Opinion of the International Searching Authority for corresponding PCT/EP2020/084228, dated Mar. 31, 2021.

Alqahtani et al, "A review on the use of additive manufacturing to produce lower limb orthoses", Progress in Additive Manufacturing, vol. 5, No. 2, Nov. 8, 2019 (Nov. 8, 2019), p. 85-94. (See Written Opinion for description of relevance).

* cited by examiner

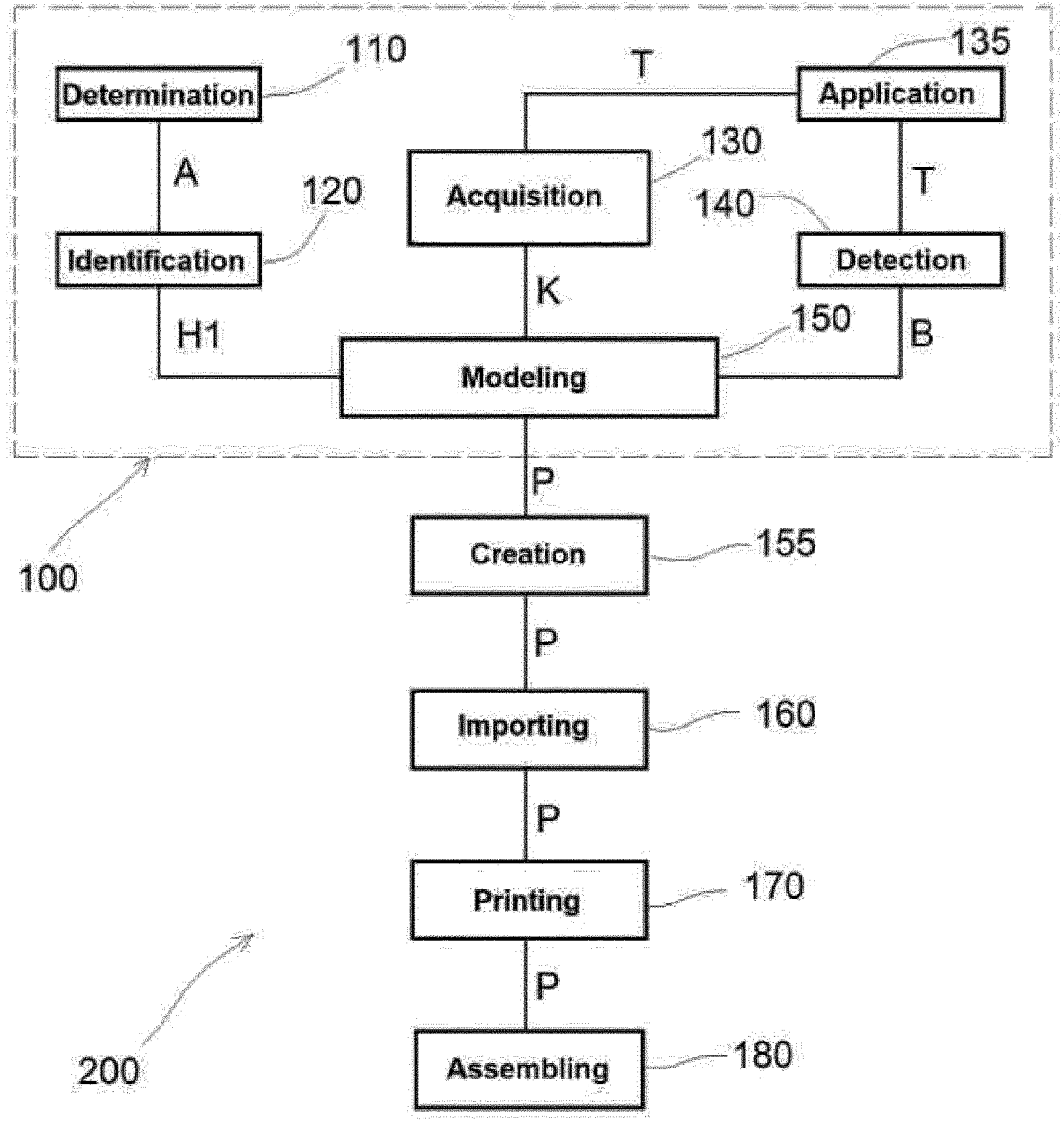

REALIZATION METHOD OF AN ORTHOPEDIC SUPPORT

The present patent application for industrial invention relates to a design method and to a realization method of an orthopedic support.

In particular, the field of application of the present patent application for industrial invention is the medical field for the realization of orthopedic supports that are used to immobilize limbs or anatomical parts following to fractures or for the realization of implantable internal prostheses.

As it is known, a fracture of a limb is usually treated by means of a traditional plaster in order to immobilize the limb or the anatomical part of the patient that has suffered the injury or fracture.

Such a solution is not the ideal solution for a patient because the plaster applied to the injured or fractured limb is not waterproof and causes excessive perspiration, skin irritation and bad odors. Moreover, the plaster is extremely heavy and bulky and hinders the free movement of the patient, who cannot lead an adequate lifestyle.

Inventors, doctors and engineers have constantly worked throughout the years to find a better solution than the plaster according to the prior art.

An alternative solution consists in using a generic brace that can be purchased in an orthopedic medical supplies store. Such generic braces are very expensive, and they are not always functional and suitable for all types of injuries or fractures.

The suppliers of said traditional braces must store large quantities in order to offer all sizes to satisfy the requirements of users with a different physical configuration.

An alternative solution consists in the realization of 3D-printed custom supports that are extremely difficult to realize and require a long time to be produced. More precisely, said custom supports provide for scanning the injured part of the body in order to obtain a 3D image. Successively, such a 3D image is modified by a designer or specialized user with a CAD software in order to obtain a 3D prototype of the support. The modification of the 3D image by the designer or specialized user is an extremely long and complicated operation. Evidently, such a long processing time is not compatible with patients who need said supports very urgently.

WO2017127887A1 discloses a method and system for producing a digital model of a customized device, comprising the steps of: importing a first digital file of a base part; importing a second digital file of a target shape; determining a warping interpolation function based on source point positions associated with the base part and target point positions associated with the target shape; and applying the warping interpolation function to the points of said base part to generate a model of said customized device.

US2015328016A1 discloses a custom modular device and a method for fabricating the custom device that includes marking a body with reference points and/or other indicators. Multiple images of the body from multiple angles are then obtained. The images are used to determine the contours of the body and the other markings are located and used to design a brace having an inner surface that corresponds to the contours of the body. The custom modular brace is fabricated as multiple pieces that are releasably coupled together and sequentially removed as the patient heals.

The purpose of the present invention is to overcome the drawbacks of the prior art by disclosing a design method of an orthopedic support used to rapidly and easily design an orthopedic support for a patient An additional purpose of the present invention is to disclose a realization method of an orthopedic support used to rapidly and easily realize a custom orthopedic support for a patient.

These purposes are achieved according to the invention with the characteristics of the appended independent claim 1.

Advantageous embodiments appear from the dependent claims.

The method according to the invention is defined by claim 1.

For the sake of clarity, the description of the design method and of the realization method of an orthopedic support according to the present invention continues with reference to FIG. 1, which only has an illustrative, not limiting value; said FIG. 1 is a flow diagram that illustrates the realization method of an orthopedic support according to the invention.

With reference to FIG. 1, the design method of an orthopedic support according to the present invention is disclosed, which is indicated with the reference numeral (100), together with the realization method of an orthopedic support, which is indicated with the reference numeral (200).

The orthopedic support designed with the design method (100) and successively realized with the realization method (200) is suitable for being applied on a part (A) of the body or on a limb of a patient in such a way to temporarily immobilize said part (A) of the body in order to heal said part (A) of the body.

The design method (100) of the orthopedic support provides for a step of determination (110) wherein a doctor or an expert technician determines the part (A) of the patient's body where the orthopedic support is to be applied.

After determining such a part (A) of the patient's body, a step of identification (120) is performed, wherein a generic 3D model (H1) of a support relative to the part (A) of the patient's body where the orthopedic support is to be applied is identified in a database of 3D models.

The database contains a plurality of generic 3D models (H1), each one corresponding to a given part (A) of the body and to a specific type of injury or fracture.

The generic 3D models (H1) stored in the database are previously realized and loaded by a doctor, a biomedical engineer, a 3D modeling designer or a specialized operator.

Preferably, each generic 3D model (H1) stored in the database of 3D models comprises a plurality of base units that are connected one to the other to define said generic 3D model (H1). The base units of the generic 3D model (H1) are disposed in such a way to define separation lines between adjacent base units that coincide with stress lines and breakage lines of the generic 3D model (H1).

After identifying the generic 3D model (H1) that corresponds to the part (A) of the patient's body, a step of acquisition (130) is performed by means of 3D image acquisition means in order to acquire a 3D image (K) of the part (A) of the patient's body where the orthopedic support is to be applied.

Preferably, said step of acquisition (130) is performed by means of any imaging diagnostic process using an X-Ray, CT, CAT, nuclear magnetic resonance apparatus, 3D scanner, laser scanner or the like.

Alternatively, said step of acquisition (130) can be performed by means of one or more cameras that generate 2D photographs of the part (A) of the patient's body from different viewpoints and different angles.

If the step of acquisition is performed by taking a plurality of 2D photographs generated by a camera or by multiple cameras, in such a case a step of reconstruction of the 3D image from the 2D photographs must be performed. In such a step of reconstruction of the 3D image, a photogrammetric technique known as Structure From Motion (SFM) is preferably used, it being a computer vision technique used to generate 3D models from 2D photographs wherein an object is framed from multiple viewpoints and different rotation angles.

Such a photogrammetric technique used to perform said step of reconstruction of the 3D image (K) provides for the following steps:

extraction of features (key points) from the 2D photographic images; said features consisting in points of a photographic image with a high possibility of being identified in other 2D photographic images of the same object; for example, said features may consist in angles, corners, or sharp color changes in the 2D photographic image;

matching of the features in each pair of 2D photographic images;

calculation of the position and of the photographic parameters of the camera for each 2D photographic image in such a way to position the features in a 3D space, generating a dispersed cloud of points;

densification, wherein the density of the dispersed cloud is increased, generating a dense cloud;

construction of a continuous surface that interpolates the points of the dense cloud, generating a "mesh", namely the 3D image (K).

Such a photogrammetric technique, which allows for reconstructing the 3D image (K) from 2D photographs, is cheaper than the 3D scanning techniques and does not require the use of special devices, except for an ordinary digital camera.

The 3D image (K) of the injured part (A) of the body is stored in digital format as 3D model.

After acquiring the part (A) of the patient's body and after generating the 3D image (K), a step of detection (140) of biometric data (B) of the part (A) of the body is performed. In the step of detection (140), biometric data (B), such as volume, length, circumference and angles of curvature, is detected from the part (A) of the patient's body.

In order to facilitate the step of detection (140) of said biometric data (B), a step of application (135) is performed before the step of detection (140) to apply markers (T) on the skin of the part (A) of the patient's body or visual digital markers (T) on the 3D image (K) acquired in the step of acquisition (130).

If the acquisition is performed by means of 3D laser, laser scanner or camera, then the markers (T) are applied on the skin of the part (A) before the step of acquisition (130).

For illustrative purposes, said markers (T) may consist in PVC stickers (with different color and shape). The markers are encoded with the colors or shapes of the markers, in such a way to identify different parts of the body, the beginning or the end of a limb, the direction of the acquisition, the injured point, etc.

The markers (T) can be also used to identify positions of holes that the doctor or the specialized technician wants to have in the final orthopedic support.

The markers can also be generated previously and rigidly stored in the database of the generic 3D models (H1) as known points that are made available for the acquisition.

Instead, if the 3D image comes from an X-Ray, CT, CAT and/or nuclear magnetic resonance apparatus, a specialized operator will introduce digital markers (T) (landmarks) directly in the acquired 3D image (K). In such a case, evidently, said step of application (135) will be performed after the step of acquisition (130).

The step of detection (140) provides for calculating the relative distances between the markers (T) and the relative positions between the markers (T) in such a way to determine said biometric data (B) (volumes, length, angles of curvature) of the part (A) of the patient's body.

A step of modeling (150) of the generic 3D model (H1) is provided after the step of acquisition (130) and the step of detection (140).

Said step of modeling (150) provides for:

a step of merging, wherein the generic 3D model (H1) is merged with the 3D image (K) in such a way to obtain a 3D model that is modelized according to the morphology of the part (A) of the patient's body;

a step of dimensioning wherein the modelized 3D model is redimensioned based on the biometric data (B) extracted in the step of detection (140), in such a way to obtain a 3D digital prototype (P) of the orthopedic support.

More precisely, during said step of modeling (150), each base unit of the generic 3D model (H1) is modelized and redimensioned based on the biometric data (B) detected in the step of detection (140).

The step of merging provides for adapting the generic 3D model to the 3D image (K) by means of shape modeling algorithms conjugated with active shape model (ASM) algorithms, Meyer's flooding algorithms, spanning forest algorithms, or other image recording algorithms that are appropriately implemented. These algorithms are used to merge the generic 3D model with the 3D image (K).

Otherwise said, the generic 3D model (H1) is overlapped to the 3D image (K) that is acquired or scanned and the generic 3D model (H1) is adjusted and modified based on the configuration of the acquired part and on the biometric data (B) determined in the step of detection (140).

After realizing the 3D digital prototype (P) of the orthopedic support, a step of creation (155) is performed to realize an STL file or a DWG file of the 3D digital prototype (P) that can be stored in a memory unit of a PC or a smart device.

If the orthopedic support is to be physically realized, after storing said 3D digital prototype (P), a realization method (200) of the orthopedic support must be performed after the design of the 3D digital prototype (P).

The realization method (200) of the orthopedic support provides for performing all the steps that were previously described in the design method, and for performing the following operating steps:

a step of importing (160) the 3D digital prototype (P) in a 3D printer; during such a step, the 3D digital prototype (P) is loaded on a software that is commonly defined as SLICER, which sets the data and the parameters for the 3D printer and saves the 3D digital prototype (P) in G-code format;

a step of printing (170) the 3D model of the orthopedic support with the 3D printer in such a way to obtain said orthopedic support.

Considering that the initial generic 3D model (H1) is composed of a plurality of base units, a plurality of elements is printed during the step of printing (170), each element corresponding to a base unit of the initial generic 3D model (H1). After being printed, during a step of assembling (180), all the elements are assembled around the part (A) of the patient's body by means of adjustable fixing means in such a way to adjust the mutual position of the elements that were printed during the step of printing (170). The possibility of adjusting the mutual position of the elements guarantees the versatility and adjustability of the orthopedic support to the needs of the patient during the various steps of the injury.

The adjustable fixing means may comprise a connection screw or an Archimedean screw to ensure accurate adjustment.

Alternatively, the elements can be fixed by means of simple tooth, backward tooth, double tooth, dovetail, male-female couplings, or other appropriate connection.

The connections used for the elements may vary according to the type of stress suffered during operation and according to the material used. For illustrative purposes, if traditional fit-in couplings are used, after the machining of contact surfaces, the stress will be directly transmitted by compression. If mechanical connections are used, by inserting mechanical and/or plastic elements to connect the adjacent elements, the stress will be indirectly transmitted.

The mechanical elements used to indirectly connect the elements can be connectors with cylindrical stem (nails, pins, screws and cramps) or surface connectors (pegs, rings and toothed plates).

Preferably, the initial generic 3D model (H1) stored in the database is provided with holes.

The holes define openings of the 3D digital prototype (P) after the modeling of the generic 3D model (H1) in the step of modeling (150).

Therefore, also the final orthopedic support that is printed during the step of printing (170) is provided with openings.

Such openings can be used to have access to the patient's skin in order to apply sensors that communicate with a smartphone or other devices in such a way to detect biomedical signals and monitor the patient from remote.

Alternatively, said openings can be used to have access to the patient's skin in order to apply devices that release anti-inflammatory substances, or to apply electrodes that stimulate the part (A) of the patient's body in such a way to accelerate and improve the patient's healing.

Preferably, the step of printing (170) of the final orthopedic support is performed with a polymeric material, such as polylactic acid (PLA), acrylonitrile butadiene styrene (ABS), ALLUMIDE or the like, Titanium (Ti Gr1) or other alloys.

Additionally, the orthopedic support can be realized with multiple types of polymeric material/alloy based on the structural, mechanical and functional characteristics of the orthopedic support.

The advantages of the present invention are manifest after the preceding description.

In fact, the provision of the database of generic 3D models (H1) considerably accelerates the design and the realization of the orthopedic support, diversifying the orthopedic supports based on the morphology of the part (A) of the body, and on the specific type of injury, fracture or deficit of the part (A) of the patient's body.

Moreover, the advantages of the orthopedic support obtained with the afore-described realization method (200) of the orthopedic support include adjustability, perspiration, rapid production and use of economic, recyclable materials.

Although the present description refers to methods for the design and the realization of an orthopedic support, the same advantages can be obtained if said methods are used to realize implantable internal prostheses that exactly reproduce the internal part of the patient that is missing or injured, without altering the articular movement, guaranteeing a faster, easier functional recovery. Said internal prostheses can be applied in all the districts of the skeleton, including small joints and vertebrae.

Additionally, said methods can be also used to design or realize generic wearable objects, such as hats, bracelets or rings, or to realize scaffolds in tissue engineering, or to realize 3D scaffolds used in cellular cultures for the growth and proliferation of eukaryote and/or prokaryote cells.

Numerous equivalent variations and modifications, which are within the reach of an expert of the field and fall in any case within the scope of the invention as disclosed by the appended claims, can be made to the present embodiment of the invention.

The invention claimed is:

1. A method for forming an orthopedic support for a body, the method comprising:

determining a portion of the body to which the orthopedic support is to be applied;

identifying of generic three-dimensional model in a three-dimensional model database relative to the portion of the body to which the orthopedic support is to be applied;

acquiring of a three-dimensional image of the portion of the body to which the orthopedic support is to be applied by a three-dimensional acquisition system;

detecting biometric data of the portion of the body to which the orthopedic support is to be applied;

merging the generic three-dimensional model with the three-dimensional image so as to obtain a three-dimensional model that is modelized in accordance with a morphology of the portion of the body, the step of modeling comprising:

redimensioning the modelized three-dimensional model according to biometric data detected in the step of detecting so as to obtain a three-dimensional digital prototype of the orthopedic support, wherein each generic three-dimensional model stored in the three-dimensional model database has a plurality of base units that are joined together, wherein each base units of the plurality of base units being redimensioned in accordance with the biometric data detected in the step of detecting, wherein the plurality of base units of the generic three-dimensional model are disposed so as to define separation lines between adjacent base units of the plurality of base units that coincide with stress lines and breakage lines of the generic three-dimensional model, wherein the generic three-dimensional model stored in the three-dimensional model database has holes, the holes defining openings of the three-dimensional model prototype after the step of modeling of the generic three-dimensional model, wherein the method further comprises:

importing of the three-dimensional digital prototype into a three-dimensional printer;

printing of the three-dimensional orthopedic support with the three-dimensional printer, wherein a plurality of elements is printed during the step of printing, each element of the plurality of elements corresponding to a base unit of the generic three-dimensional model; and assembling the plurality of elements around the portion of the body by an adjustable fixer so as to adjust a mutual position of the plurality of elements printed during the step of printing.

* * * * *